United States Patent [19]

Abraham et al.

[11] Patent Number: 4,799,480
[45] Date of Patent: Jan. 24, 1989

[54] ELECTRODE FOR ELECTROSURGICAL APPARATUS

[75] Inventors: William W. Abraham, New Hartford; John S. Gentelia, Madison, both of N.Y.

[73] Assignee: Conmed, Utica, N.Y.

[21] Appl. No.: 81,154

[22] Filed: Aug. 4, 1987

[51] Int. Cl.⁴ ............................................. A61B 17/39
[52] U.S. Cl. ................................. 128/303.13; 128/798
[58] Field of Search ................ 128/303.13, 798, 802, 128/803

[56] References Cited

U.S. PATENT DOCUMENTS

| | | | |
|---|---|---|---|
| 3,848,600 | 11/1974 | Patrick, Jr. et al. | 128/303.13 |
| 4,067,342 | 1/1978 | Burton | 128/798 |
| 4,387,714 | 6/1983 | Geddes et al. | 128/303.13 |

FOREIGN PATENT DOCUMENTS 1092420  4/1955  France ................................. 128/798

Primary Examiner—Lee S. Cohen
Attorney, Agent, or Firm—Larson & Taylor

[57] ABSTRACT

An electrode for use with electrosurgical apparatus is provided which establishes capacitive coupling with the skin of a patient. The electrode includes a conductive plate connected to the electrosurgical apparatus with an insulating layer disposed in contact with the conductive plate and on the opposite face of the insulator there is provided conductive material in the form of a plurality of discreet islands of conductive adhesive material. The islands of conductive adhesive material are in contact with the skin of the patient and provide a plurality of independent current paths providing substantially uniform current flow from each element of the skin in contact with the islands of conductive material.

8 Claims, 1 Drawing Sheet

ELECTRODE FOR ELECTROSURGICAL APPARATUS

FIELD OF THE INVENTION

The invention relates to an electrode for electrosurgical apparatus or similar high current, skin connected current source which provides interface with the body of a patient and this interface provides more uniform current conduction and a reduction in hot spots in the areas in which the electrode is in contact with the patient's skin.

BACKGROUND OF THE INVENTION

The use of dispersive type electrodes in connection with electrosurgical or body stimulation apparatus is well known and these electrodes are used as current paths or grounding pads to provide conducting paths between the patient and the stimulation or electrosurgical equipment. While these electrodes can be used for any skin conducting application where currents may be high enough to cause heating only the electrosurgical application will be described for simplicity.

At present, disposable electrosurgical dispersive electrodes divide into two general groups, those electrodes which provide a conductive interface with the body of a patient and those electrodes which provide a capacitive interface with a patient's body.

The conductive dispersive electrodes are more generally used and comprise a metal plate held in contact with a patient's skin, often with a jelly-like electrolyte or by use of a conductive adhesive which is disposed between the metallic electrode and the skin of the patient. The problem with such conductive electrodes is that generally in use there is a nonuniform temperature distribution of the skin immediately under or near the electrode for the reason that the current tends to concentrate in that skin area having the least resistance path which is generally at the edge of the electrode nearest the active electrode surgical site.

The other type of electrosurgical dispersive electrode is the capacitive type which is provided with a plastic film or like insulating area separating the conductive metal plate from the patient's skin. This arrangement provides a large impedance and a voltage drop of a capacitive nature between the skin surface and the metal electrode. When attached to completely clean, uniform skin, this type of electrode results in more equal distribution of current over the entire area of the electrode thus reducing uneven temperatures or hot spots in certain areas of the patient's skin. When such dispersive electrodes are properly applied that they are in intimate contact with the patient's skin, the large voltage drop across the dielectric film is out of phase with the current through the film resulting in practically no heat generation within the dielectric layer itself. However, considering hair and other skin irregularities it is exceedingly difficult in actual practice to provide for absolute intimate contact between the dielectric film of the capacitive dispersive electrode and the patient's skin.

The Geddes et al Pat. No. 4,387,714 discloses a hybrid type of electrosurgical dispersive electrode in which a layer of conductive adhesive is placed between the dielectric layer of a capacitive ground pad and the patient's skin. This arrangement clearly improves the intimacy of contact between the electrode and the patient's skin. However, it has been found in practical use that the layer of conductive adhesive below the dielectric layer prevents uniform current dispersion provided by a capacitive dispersive electrode. When all of the elements of the patient's skin surface are tied together with a continuous sheet of conductive adhesive, the freedom of each element of the patient's skin to see the high impedance current source which is provided by the corresponding element of the dielectric capacitor action is lost. Instead, the result is similar to connecting a capacitor in series with a normal conductive type dispersive electrode. Nonuniform heating of the tissue under and near the described hybrid dispersive electrode is the result, very similar to that obtained with the usual conductive dispersive electrode.

SUMMARY OF THE INVENTION

The present invention provides an improved electrosurgical dispersive electrode comprising a conductive plate having an insulator layer extending across the entire face of the plate with a plurality of discrete conductive adhesive elements forming islands on the side of the insulator opposite to the conductive plate. There is little or no lateral conduction between the islands of conductive adhesive and the size of the islands is chosen to achieve the desired degree of uniformity of temperature rise across the dispersive electrode.

By utilizing electrically independent conductive adhesive islands to separate the dielectric layer covering the metal electrode plate, each skin area has an independent high impedance and a lossless current path enabling substantially uniform current flow from each element of the skin. This uniform current flow exists even though the resistance from the various elements of skin surface into the core tissue of the body may be substantially different for different areas. The resistances through the various skin elements are small compared with the impedance of the individual capacitor elements which connect the skin surface areas to the metal electrode plate.

It is an object of the present invention to provide an improved dispersive electrosurgical electrode. It is a further object of the present invention to provide an electrode which is a collection of small discrete areas of moderately high but lossless impedance, coupled to small areas of skin, which provides a more uniform and lower temperature rise in the skin area associated with the dispersive electrode.

It is still another object of the present invention to provide an electrode having a metal electrode plate with an insulator thereon and a plurality of discrete conductive islands of adhesive material in engagement with the insulating layer.

Other objects and many of the attendant advantages of the present invention will become more readily apparent upon consideration of the following detailed specification when considered in connection with the accompanying drawings wherein:

FIG. 1 is a plan view of an electrode in accordance with the present invention; and FIG. 2 is a cross-sectional view along the lines 2—2 of FIG. 1 of the dispersive electrode according to the present invention.

DETAILED DESCRIPTION OF THE INVENTION

Figure 1:
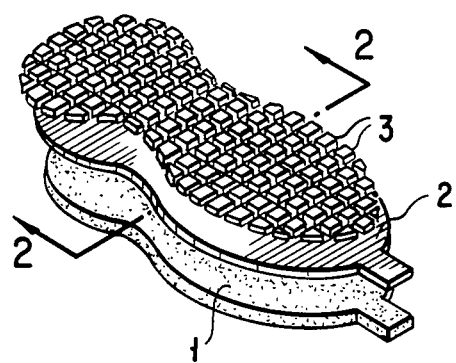
Figure 2:
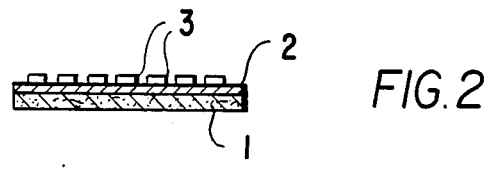

The dispersive electrode according to the present invention comprises a conductive plate 1 which may be of foil or deposited conductive material having an insulator 2 fixed to one surface thereof. The insulator 2 is of a film thickness of from 2 micron to 75 microns which is selected so that at the overall pad area chosen so that the voltage drop across the film is between 5 and 300 volts at one ampere of ground pad current and is preferably about 70 volts so as to enable equalization of current between the conductive adhesive segments referred to hereinafter, without excessive voltage drop which would tax this output voltage capabilities of the electrosurgical generator equipment.

Suitably secured to the surface of the insulator 2 opposite the conductive layer 1 are a plurality of individual conductive islands 3 which are of a conductive adhesive or conductive gel presently used with grounding pads of the conductive type. The islands of conductive adhesive or conductive gel are sufficiently small to have essentially uniform total impedance from the electrode surface to the core of the body. A range in size of 0.1 $cm^2$ to 10 $cm^2$ conductive adhesive areas which are arranged in near touching relationship appears to achieve the desired relationship.

The presently disclosed electrosurgical dispersive electrode provides significant advantages over prior art electrodes. Conventional ground pads provide a single layer of high conductivity gel or conductive adhesive over a metal electrode. This particular combination is subject to local hot areas during high current electrosurgery for the reason that the current tends to concentrate at the edge of the pad nearest the site of the surgical operation or in areas where there is good blood flow and low resistance in the body tissues. The extra heating which occurs in the tissue where the current is concentrated requires an excessive area for the pad so that the areas of current concentration are still cool enough to avoid damage to the patient's skin. Current takes the path of least resistance and the heat produced in each area of the tissue is proportional to the real or resistance part of its impedance multiplied by the local current squared. Thus, the tissue and conductive gel adhesive are mostly resistive so the current increases linearly in areas of smaller resistance and these effects reduce the resistance in the heat generation equation but increase the current so that the net effect is to produce more heat in areas of lower resistance.

As noted hereinbefore, the Geddes U.S. Pat. No. 4,387,714 adds a low loss capacitive film between the metallic electrode and the conductive gel or conductive adhesive layer. This is intended to provide a lossless reactive impedance in series with each area of the tissue, the impedance being of large magnitude in comparison with the differences in path resistance thus serving to dilute the differences and restoring current flow to near equality in all areas of the current path from the surgical site to the ground pad electrode. However, it has been found that lateral currents in the highly conductive gel or adhesive restore the unipotential nature of the metallic electrode beneath the capacitive layer. The effect is somewhat similar to connecting one capacitor in series with, but external to the conventional conducting type of ground pad. This arrangement would simply provide a useless extra voltage drop in series with the dispersive electrode, leaving the uneven distribution of currents in the tissue beneath. However, if the conductive gel or conductive adhesive between the ground pad electrode and the tissue is divided into electrically isolated islands under the low loss dielectric layer, separate capacitors are, in effect, connected in series with each area. This produces a current equalizing effect and allows the actual voltage at each area of the tissue surface to be different, thus equalizing the current flow from each area.

Obviously, many modifications and variations of the present invention are possible in light of the foregoing teachings.

What is claimed as new and desired to be secured by Letters Patent is:

1. A skin current conducting electrode comprising a conductive element adapted to be connected to a current generating unit, an insulator having one surface thereof in contact with one entire surface of said conductive element, a plurality of discrete conductive elements disposed on the opposite surface of said insulator whereby when said discrete conductive elements are disposed in contact with the skin of a patient each area of the skin of a patient contacted by the individual conductive element forms a largely independent current path.

2. A skin current conducting electrode according to claim 1 wherein said discrete conductive elements are formed of conductive adhesive material to adhere individually to discrete skin areas of a patient.

3. A skin current conducting electrode according to claim 1 wherein said discrete conductive elements are formed of conductive gel.

4. A skin current conducting dispersive electrode according to claim 1 wherein said discrete conductive elements range in size from 0.1 to 10 $cm^2$.

5. A skin current conducting electrode according to claim 1 wherein said insulator comprises a plastic film having a thickness of from 1 to 75 microns.

6. A skin current conducting electrode according to claim 1 wherein said conductive element comprises a foil plate.

7. A skin current conducting electrode according to claim 1 wherein said conductive element comprises a conductive film deposited on said insulator.

8. A skin current conducting electrode according to claim 1 wherein said discrete conductive elements comprise conductive adhesive islands of approximately 1 $cm^2$.

* * * * *